United States Patent [19]

Waggott

[11] 4,290,435

[45] Sep. 22, 1981

[54] INTERNALLY COOLED ELECTRODE FOR HYPERTHERMAL TREATMENT AND METHOD OF USE

[75] Inventor: David Waggott, Woodside, Calif.

[73] Assignee: Thermatime A.G., Zug, Switzerland

[21] Appl. No.: 74,400

[22] Filed: Sep. 7, 1979

[51] Int. Cl.³ .............................................. A61N 1/04
[52] U.S. Cl. ..................................... 128/800; 128/804
[58] Field of Search .................. 128/804, 783, 419 R, 128/422, 399, 400, 800

[56] References Cited

U.S. PATENT DOCUMENTS

| | | | |
|---|---|---|---|
| 1,531,414 | 3/1925 | Ruben | 128/399 |
| 3,307,553 | 3/1967 | Liebner | 128/400 |
| 4,121,592 | 10/1978 | Whalley | 128/804 X |
| 4,140,130 | 2/1979 | Storm | 128/804 X |

FOREIGN PATENT DOCUMENTS 1086062  2/1955  France ................................ 128/804

OTHER PUBLICATIONS

Lehmenn et al., "Evaluation—Contact Applicator", Arch. Phys. Med. and Rehab., Mar. 1970, pp. 143-146.

Primary Examiner—Lee S. Cohen
Attorney, Agent, or Firm—Fitch, Even, Tabin, Flannery & Welsh

[57] ABSTRACT

An improved electrode and method of use are disclosed in connection with hyperthermal treatment of tumors in humans and animals wherein a radio frequency current is caused to flow between a pair of the electrodes and through a body portion containing the tumor. The electrode assembly includes a fluid conduit in thermally conductive relation with an electrically conductive electrode in the assembly as well as jets arranged about the periphery of the conductive electrode for cooling surrounding surface portions of the body during the hyperthermal treatment. The conductive electrode is connected with a circuit for producing the radio frequency current.

8 Claims, 9 Drawing Figures

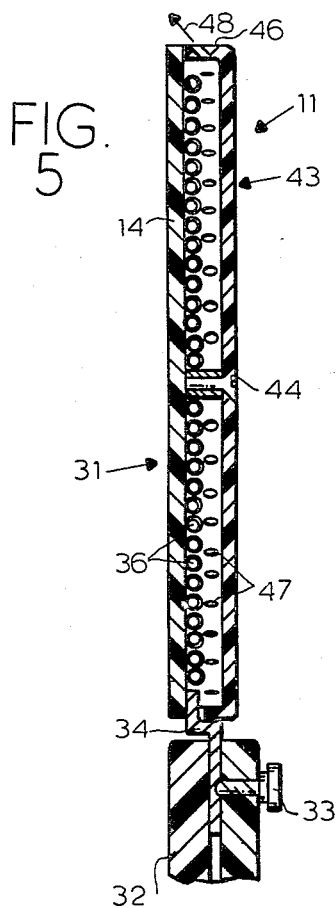
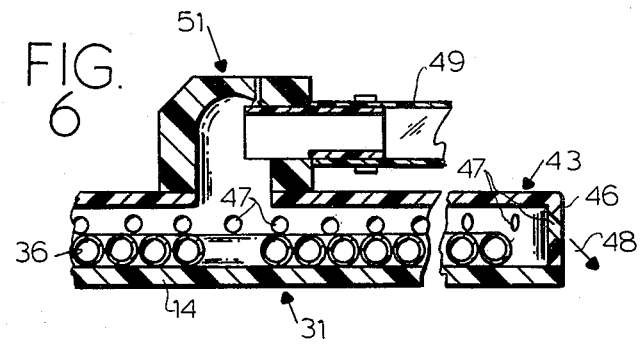
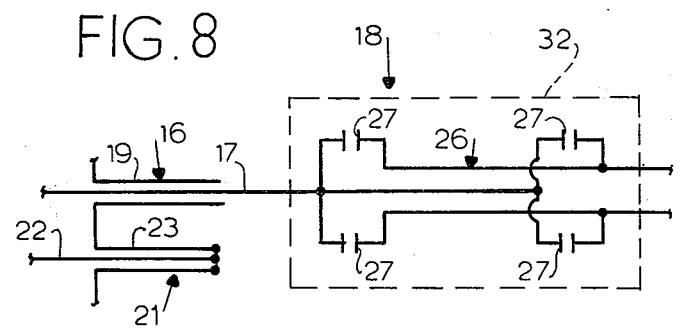
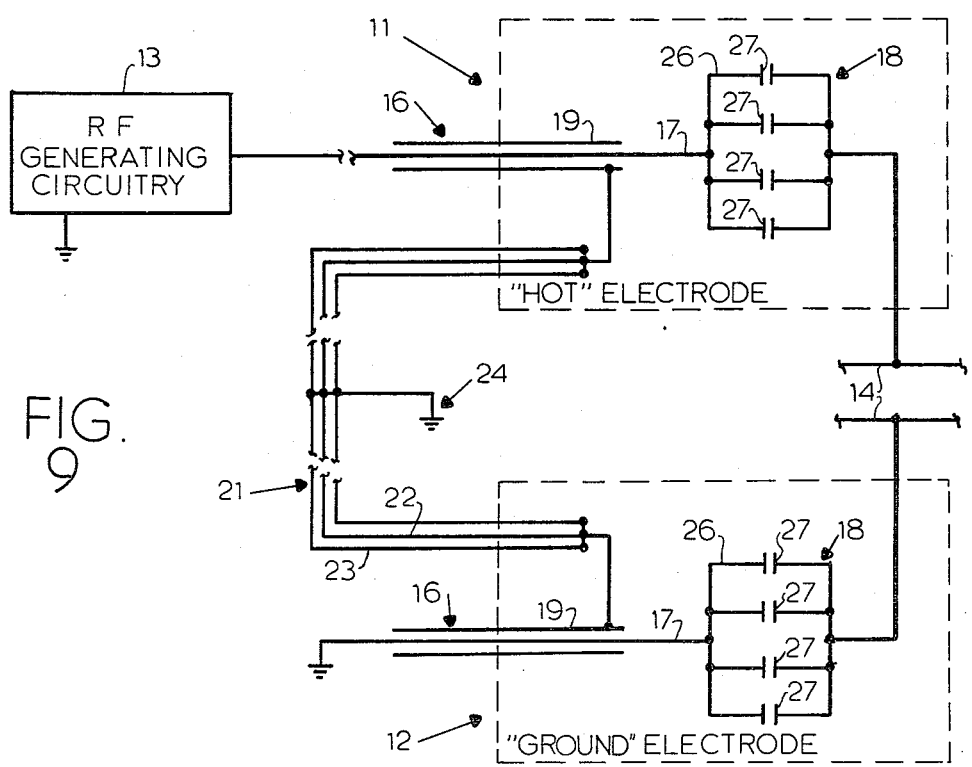

INTERNALLY COOLED ELECTRODE FOR HYPERTHERMAL TREATMENT AND METHOD OF USE

The present invention relates to an improved electrode and method of use in hyperthermal treatment of tumors in humans and animals and more particularly to such an improved electrode assembly and method of use for countering undesirable heating effects in the surface portions of the body beneath the electrode and in the area surrounding the electrode.

A method and apparatus for hyperthermal treatment of tumors by developing radio frequency currents in the tumor and surrounding tissue between electrodes contacted with adjacent surface portions of the body is disclosed in U.S. patent application Ser. No. 890,693 entitled METHOD AND APPARATUS FOR HEATING TISSUE and filed on Mar. 27, 1978 by Wilfrid B. Whalley, now U.S. Pat. No. 4,237,898. Very generally, the method and apparatus of that application comprises the use of radio frequency oscillator means and amplifier means coupled to the output of the radio frequency oscillator means for producing an amplified radio frequency output signal. The application further describes electrode means which are coupled to the amplifier means and include insulated conductive electrodes having a configuration adapted to transmit an electric current directly into the tissue to which they are attached for passing current through both the tumor and surrounding tissue. Additional means are provided for controlling the power of the amplifier means to avoid heating the surrounding tissue beyond a preselected temperature level while causing the tumor to heat beyond the preselected temperature level over a selected duration of time in order to cause substantial necrosis of the tumor while avoiding damage to the surrounding tissue.

The above-noted application includes various parameters for such a method of hyperthermal treatment which are incorporated by reference herein but which are not essential to an understanding of the construction of the improved electrode and method of its use toward which the present invention is specifically directed. Accordingly, it will be apparent from the following description that the improved electrode assembly described herein may be employed to advantage within the method and apparatus of the above-noted reference.

During operation of the method and apparatus of the above-noted reference, substantial heating effects develop which must be controlled or countered in order to avoid undesirable heating of surface portions of the body. In particular, the surface portions of the body, beneath and surrounding the conductive electrodes, are subject to heating effects because of the radio frequency currents being passed therethrough. It is desirable to minimize heating of the surface portions of the body in order to avoid damage to the skin or other surface portions of the body. In addition, it is also desirable to maintain temperatures of the surface portions of the body within selected limits of comfort in order to avoid the need for using anaesthetics during the hyperthermal treatment. Avoiding the use of anaesthetics permits the patient to indicate the response of his body to the hyperthermal treatment and to assist in better regulating operating parameters for treatment.

SUMMARY OF THE INVENTION

It is accordingly an object of the present invention to provide an improved electrode assembly and method of its use for applying radio frequency currents to selected body portions in a method of hyperthermal treatment as disclosed above while countering or minimizing heating effects in surface portions of the body. It is a more specific object of the invention to provide means in heat exchange communication with the surface of the body at the area of contact with each electrode assembly in order to minimize heating effects originating within surface portions of the body. At the same time, additional heat exchange means are arranged adjacent the periphery of the conductive electrode for cooling surface portions of the body immediately surrounding the conductive electrode during the hyperthermal treatment.

It has been discovered that during use of such electrode assemblies in hyperthermal treatment, heating results not only in the tissue directly beneath the conductive electrode but also in surface portions of the body which are not overlaid by the conductive electrodes but rather which surround peripheral portions of the electrodes. Heating of such surrounding surface portions of the body may result from edge effects of the electrodes as well as the tendency to develop a barrel-shaped field within the body portion between the two electrodes. The first heating effect referred to above merely relates to the development of heat at the periphery of the electrode which may tend to pass into surrounding body portions. The barrel-shaped field developed between the electrodes is developed because heating of body portions intermediate the electrode is not strictly limited to an envelope formed by the peripheries of the electrodes. Rather, the heated portion of the body extends beyond that envelope in a barrel-like configuration. This barrel effect has been found to result in substantial heating of surface portions of the body surrounding the periphery of the conductive electrodes.

It is yet another object of the invention to provide improved means for interconnecting the conductive electrodes in the electrode assemblies with suitable circuit means for developing the radio frequency current and field within a body portion containing a tumor.

Additional objects and advantages of the invention are made apparent in the following description having reference to the accompanying drawings.

BRIEF DESCRIPTION OF THE DRAWINGS

FIG. 5 is a view taken along section line V—V of FIG. 1.

FIG. 6 is a fragmentary view taken along section line VI—VI of FIG. 1.

FIG. 8 is a schematic representation of electrical circuitry forming a portion of the electrode assembly.

FIG. 9 is a schematic representation of a pair of electrode assemblies constructed in accordance with the present invention and suitably interconnected with electronic circuitry for developing a radio frequency field between the electrode assemblies.

BRIEF DESCRIPTION OF THE PREFERRED EMBODIMENT

Figure 1:
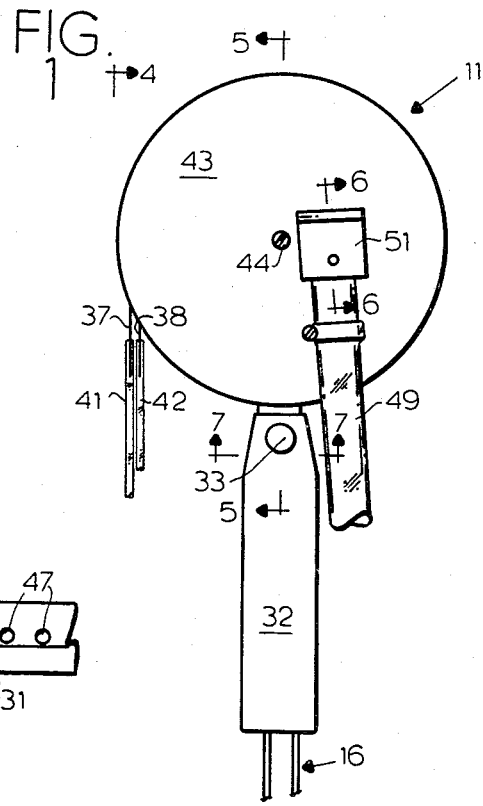
FIG. 1 is a plan view of an electrode assembly constructed in accordance with the present invention.
Figure 2:
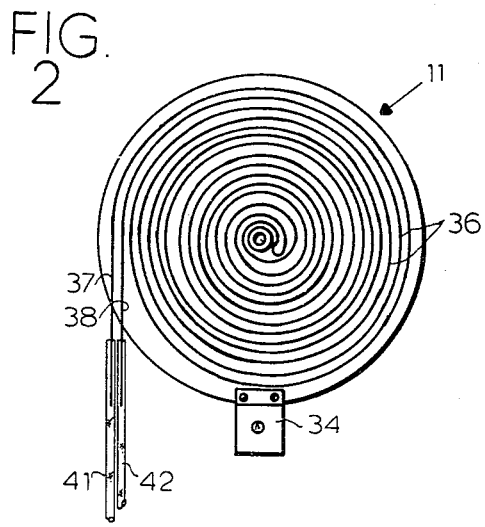
FIG. 2 is a similar view of the electrode assembly with its handle removed and a fluid coolant housing removed in order to better illustrate a heat exchanger for cooling the conductive electrode of the electrode assembly.
Figure 7:
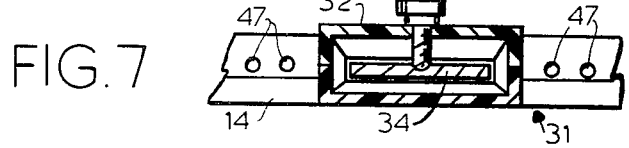
FIG. 7 is a view taken along section line VII—VII of FIG. 1.

As was indicated above, the present invention relates to an improved electrode and method of its use in hyperthermal treatment of tumors and the like in humans and animals. The combination of suitable radio frequency generating circuitry and the configuration of conductive electrodes for developing a radio frequency field in the area of a tumor to be treated were also discussed in detail in the above-noted reference which is accordingly incorporated herein by reference particularly to provide a disclosure of the radio frequency generating circuitry and additional details concerning the hyperthermal treatment itself.

As disclosed within the above-noted reference and contemplated by the present invention, a pair of electrode assemblies are arranged on opposite surfaces of a body portion containing a tumor to be treated. The electrodes are connected with radio frequency generating circuitry suitable for producing the radio frequency field including the tumor to be treated. The radio frequency generating circuitry which is clearly disclosed by the above reference comprises generally a radio frequency oscillator means and amplifier means coupled to the output of a radio frequency oscillator means for producing an amplified radio frequency output signal. Conductive electrodes in the respective electrode assemblies are suitably connected with the amplifier means and include insulated conductive electrodes having a configuration adapted to pass an electric current directly into the tissue to which they are attached in order to cause the current to pass through the tumor to be treated as well as surrounding tissue of the body.

Means are provided for controlling the power of the amplifier means in order to minimize or limit heating of the surrounding tissue to no more than a preselected temperature level while causing the tumor to heat beyond the preselected temperature level. Because the blood circulation rate and hence the cooling effect in the tumor is substantially lower than that in the healthy surrounding tissue, the tumor heats to a higher temperature which even further decreases circulation within the tumor. By carefully selecting the predetermined upper temperature limit for the surrounding tissue and/or for the body as a whole, for example, 104° F. as measured orally, the current may be regulated so that the surrounding tissue does not exceed the predetermined temperature level. However, the temperature of the tumor is caused to exceed that predetermined temperature level because of the effects noted above and maintained at that temperature for a sufficient predetermined period of time in order to completely or partially destroy the tumor.

As was noted above, greater detail concerning both the radio frequency generating circuitry and the method of hyperthermal treatment is discussed in greater detail in the above-noted reference. For purposes of the present invention, it is sufficient to understand that suitable radio frequency generating circuitry may be interconnected with a pair of electrode assemblies for accomplishing the hyperthermal treatment. Referring momentarily to FIG. 9, electrode assemblies indicated respectively at 11 and 12 are interconnected with radio frequency generating circuitry generally indicated at 13. The electrode assemblies both include conductive electrodes 14 between which a radio frequency field is developed in order to accomplish hyperthermal treatment as outlined above. Before proceeding with a more detailed description of the electrode assemblies, it is noted with reference to FIG. 9 that they are of generally similar construction except that the electrode assembly 11 is preferably connected directly with the RF generating circuitry 13 in order to include a "hot" conductive electrode. The other electrode assembly 12 is grounded so that it includes a "ground" conductive electrode which, because of the grounding in the RF generating circuitry 13, forms a complete circuit between the electrode assemblies 11 and 12 and the circuitry 13.

Continuing with reference to FIG. 9, each electrode assembly includes a coaxial conduit 16 having its axial conductor 17 interconnected with the respective conductive electrode 14 through a capacitor means 18. As is clearly indicated in FIG. 9, the axial conductor for the electrode assembly 11 is directly interconnected with the RF generating circuitry 13 while the axial conductor 17 for the other electrode assembly 12 is grounded. Otherwise, the electrode assemblies 11 and 12 are of substantially similar construction. Accordingly, the following description is specifically directed toward one of the electrode assemblies, particularly that indicated at 11, while also applying to the other electrode assembly 12.

The coaxial conduit 16 for each of the electrode assemblies also includes a shield 19 which is electrically insulated from the respective axial conductor. As is described in greater detail within the above-noted reference, a flexible coaxial conduit or jumper means 21 has both its axial conductor 22 and its shield 23 electrically connected to the shields 19 for the coaxial conduit 16 of both electrode assemblies 11 and 12. Both the axial conductor 22 and the shield 23 of the coaxial jumper conduit 21 are also grounded as indicated at 24.

Each capacitor assembly or means 18 preferably includes a branched circuit 26 providing a parallel interconnection multiple capacitors 27. As described for example within the above-noted reference, the capacitor assemblies 18 may be generally selected to have a capacitive reactance approximately equal to the inductive reactance for the respective coaxial conduits or cable 16.

A preferred construction for the electrode assemblies, particularly that indicated at 11, is illustrated in greater detail within FIGS. 1-8. As was noted above, the following description also applies to the other electrode assembly 12.

Figure 4:
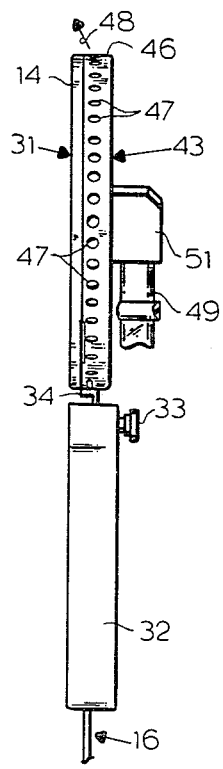
FIG. 4 is a side view of the electrode assembly of FIG. 1.
Figure 3:
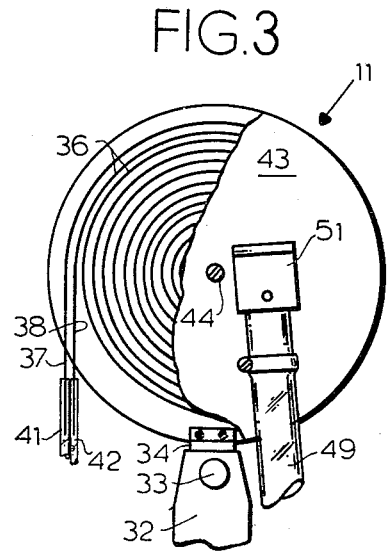
FIG. 3 is a similar view as FIG. 2 with fragmentary portions of the handle and housing being illustrated in place upon the electrode assembly.

Referring initially to FIGS. 1 and 4, the electrode assembly 11 includes a conductive electrode 14 which is formed from a smooth conductive material and has a shape suitable for the purpose of applying an electric field of a desired configuration. The conductive electrode or plate 14, as illustrated, is preferably round with its exposed surface 13 being smooth in order to facilitate transfer of the radio frequency current to the selected body portion of the patient.

A handle, 32 for better manipulating the electrode assembly is releasably attached to the electrode assembly and specifically to the conductive electrode 14 by means of a set screw 33. The set screw 33 serves to assure electrical continuity between the axial conductor 17 and a rigid conductive extension 34 forming an electrically integral portion of the conductive electrode 14. As may be best seen in FIGS. 8 and 9, the capacitor assembly 18 is arranged within the handle 32 in order to be closely adjacent the conductive electrode 14 while the respective coaxial conduit 16 provides for interconnection of the conductive electrode with the RF generating circuitry 13 and the coaxial jumper conduit 21.

In order to minimize heating of the surface portions of the body by conducting heat away through the conductive electrode 14, a hollow conduit formed from thermally conductive material is formed into a continuous coil as indicated at 36 and secured in thermally conductive relation to a rear surface of the continuous conductor 14 opposite its face 31. The coiled conduit 36 may be formed for example, from copper which is secured to the continuous conductor 14 by means of thermally conductive material such as a suitable filled epoxy. The coil 36 is preferably formed from a doubled portion of the conduit so that inlet and outlet ends 37 and 38 for the coil are arranged adjacent each other. Separate conduits 41 and 42 are respectively connected with the inlet and outlet ends 37 and 38 in order to circulate coolant through the coil 36. Water may preferably be employed as a coolant within the coil 36.

As was also discussed above, it has additionally been found important to cool a surface portion of the body lying about the periphery of the continuous conductor 14. For this purpose, a hollow housing 43 extends along the back surface of the conductive electrode 14 adjacent the coil 36 and is secured to the conductive electrode for example by means of a screw 44. A peripheral surface portion 46 of the housing 43 forms a multiplicity of jets or orifices 47 which are angularly inclined as indicated by the arrow 48 for a purpose described immediately below. A separate source of cooling fluid such as air is supplied to the interior of the housing 43 from a suitable conduit 49 which is in communication with the housing interior by means of a fixture 51. Pressurized air coolant supplied to the interior of the housing 43 from the conduit 49 passes outwardly through the orifices 47 in order to impinge and cool a surface portion of the body surrounding the periphery of the conductive electrode 14.

It is believed that a method of hyperthermal treatment including the electrode assemblies of the present invention is clearly apparent from the preceding description. However, the method of such use is briefly described in order to afford a more complete understanding of the invention.

With the two electrode assemblies being positioned with respect to the patient, a radio frequency field is developed between their conductive electrodes 14 by operation of the radio frequency generating circuit 13 (see FIG. 9). As hyperthermal treatment is carried out in accordance with the preceding summary and as also disclosed in the above-noted incorporated reference, heating effects tend to develop both within the surface portions of the body beneath the conductive electrodes 14 and within surrounding surface portions of the body in a manner described above. The electrode assembly of the present invention is adapted to counter or limit both of these heating effects throughout the entire hyperthermal treatment. Initially, cooling fluid such as water circulated through the coil 36 serves to conduct excessive heat from the surface portions of the body beneath the conductive electrodes 14. At the same time, cooling air from the conduit 49 entering the hollow housing 43 is directed outwardly through the jets or orifices 47 in order to impinge and cool surrounding surface portions of the body.

This novel dual cooling arrangement serves to better facilitate the hyperthermal treatment as well as maintain patient comfort throughout the treatment, thereby permitting the patient to better provide an indication of his body response to the treatment.

At the same time, the overall configuration of the electrode assembly, including the arrangement of the handle 32, and the manner of interconnection with the circuitry 13 and the suitable coolants for the various conduits facilitates and simplifies manipulation of the electrode assemblies.

Additional variations and modifications besides those disclosed above will be apparent and, accordingly, the scope of the present invention is defined only by the following appended claims.

What is claimed is:

1. An improved electrode assembly for use in hyperthermal treatment of tumors in humans and animals wherein the tumor and surrounding tissue is heated with radio frequency energy by applying a pair of uninsulated conductive electrodes on opposite sides of a portion of the body containing the tumor such that an electrically conductive connection is made between the electrodes and the body portion to which they are applied, a radio frequency electric alternating current being passed between the electrodes at a magnitude selected to cause heating of the tumor beyond a predetermined temperature level while minimizing heating of tissue surrounding the tumor, said improved electrode assembly comprising an uninsulated conductive plate adapted for electrically conductive engagement with a surface portion of the body including the tumor for passing an electric current through both the tumor and surrounding tissue, means for interconnecting said conductive plate with circuit means for producing said radio frequency energy, means forming passages in heat exchange communication with said conductive plate, means for circulating a fluid coolant through said passages in order to limit temperature rise within surface portions of the body beneath said conductive plate, means forming a chamber including outlet jets arranged adjacent the periphery of the conductive plate and directed outwardly of the periphery so as to be toward the surrounding surface portions of the body, and means connected with the chamber for supplying cooling fluid under pressure thereto, whereby heating in surface portions of the body immediately surrounding the conductive plate is minimized during the hyperthermal treatment.

2. The improved electrode assembly of claim 1 wherein the means forming passages comprises a continuous coil arranged within said chamber, the coil being mounted in thermally conductive relation to the conductive plate, and the means for circulating a fluid coolant having inlet and outlet means for circulating cooling fluid through the coil.

3. The improved electrode assembly of claim 1 further comprising handle means secured to said conductive plate for manipulating the plate, said handle means including conduit means for interconnecting said conductive plate with said circuit means.

4. The improved electrode assembly of claim 3 wherein said conduit means comprises at least one capacitor means forming a portion of said circuit means and arranged within said handle means in order to be closely adjacent the conductive plate.

5. The improved electrode assembly of claim 4 wherein the capacitor means arranged within the handle means comprises a parallel arrangement of multiple capacitors.

6. An improved method for hyperthermal treatment of tumors in humans and animals wherein the tumor is heated with radio frequency energy by applying a pair of uninsulated conductive electrodes on opposite exterior sides of a portion of the body containing the tumor so that an electrically conductive connection is made between the electrodes and the body portion to which they are applied, a radio frequency electric alternating current being passed between the electrodes at a magnitude selected to cause heating of the tumor beyond a predetermined temperature level while minimizing heating of tissue surrounding the tumor, the improvement comprising communicating a first cooling fluid into heat exchange contact with at least one of the conductive electrodes in order to minimize heat generation within the surface portions of the body beneath the conductive electrode due to passage of the radio frequency current therethrough and simultaneously directing additional cooling fluid to impinge surface portions of the body immediately surrounding the one conductive electrode in order to minimize heating in said surrounding surface body portions during the hyperthermal treatment.

7. The method of claim 6 wherein the first cooling fluid is passed in heat exchange contact with the one conductive electrode by means of a conductive conduit secured to a surface portion of the one conductive electrode, the additional cooling fluid being impinged upon adjacent surface portions of the body by supplying cooling fluid under pressure to a hollow housing arranged upon the one conductive electrode and including orifices about its periphery through which the additional cooling fluid may pass to impinge the surrounding body surfaces.

8. The method of claim 6 wherein cooling fluid is also communicated into heat exchange contact with the other conductive electrode while simultaneously directing additional cooling fluid to impinge surface portions of the body surrounding the other conductive electrode.

* * * * *